United States Patent [19]

Weder et al.

[11] Patent Number: 4,876,192
[45] Date of Patent: Oct. 24, 1989

[54] DETECTION OF ANTIBODIES AGAINST A CHORIONIC GONADOTROPIN-LIKE SUBSTANCE

[75] Inventors: Donald E. Weder, Highland, Ill.; Tsu T. Chi, Anaheim, Calif.

[73] Assignee: Seven W. Enterprises, Inc., Highland, Ill.

[21] Appl. No.: 112,473

[22] Filed: Oct. 22, 1987

Related U.S. Application Data

[63] Continuation-in-part of Ser. No. 778,847, Sep. 23, 1985, abandoned.

[51] Int. Cl.$^4$ .................... C12Q 1/42; G01N 33/53
[52] U.S. Cl. ......................................... 435/21; 435/7; 435/28; 436/518; 436/536; 436/540
[58] Field of Search ............... 435/7, 21, 28; 436/540, 436/518, 536

[56] References Cited

U.S. PATENT DOCUMENTS

| | | | |
|---|---|---|---|
| 4,305,924 | 12/1981 | Piasio et al. | 435/7 |
| 4,410,510 | 10/1983 | Livingstone-Wheeler et al. | 424/88 |
| 4,560,649 | 12/1985 | Saxena et al. | 436/810 |
| 4,643,970 | 2/1987 | Livingston-Wheeler et al. | 435/68 |

OTHER PUBLICATIONS

Maggio-Enzyme-Immunoassay (1980) CRC, Press, p. 61.
Maruo et al.-Chem. Abst., vol. 92 (1980), p. 90585W.
Koide et al.-Chem. Abst., vol. 94 (1981), p. 170730W.
Bahl, "Human Chorionic Gonadotropin: Purification and Physiochemical Properties", J. Biol. Chem., 244:567–574 (1969).
Livingston et al., "A Specific Type of Organism Cultivated from Malignancy: Bacteriology and Proposed Classification", Ann. N.Y. Acad. Sci., 174:636–654 (1970).
Engvall et al., "Enzyme-Linked Immunosorbent Assay (ELISA) Quantitative Assay of Immunoglobin G", Immunochem., 8:871–874 (1971).
Engvall et al., "Enzyme-Linked Immunosorbent Assay, ELISA: Quantitation of Specific Antibodies by Enzyme-Labeled Anti-Immunoglobulin in Antigen-Coated Tubes", J. Immun., 109:129–135 (1972).
Livingston et al., "Some Cultural, Immunological and Biochemical Properties of Progenitor Cryptocides", Tr. N.Y. Acad. Sci., 36:569–582 (1974).
Voller et al., "Enzyme-Immunoassays for Antibodies in Measles, Cytomegalovirus Infections and After Rubella Vaccination", Br. J. Exp. Path., 57:243–247 (1976).
Lange et al., "Suppression of Antitumor Lymphocyte Mediated Cytotoxicity by Human Chorionic Gonadotropins", J. Urol., 115:95–98 (1976).
Cohen et al., "Bacterial Synthesis of Substance Similar to Human Chorionic Gonadotropin", Proc. Soc. Exp. Biol. Med., 152:408–410 (1976).
Affronti et al., "Production of a Human Gonadotropin-Like Substance by Bacterial Tumor Isolates", Abs. Ann. Meeting Am. Soc. Micro., p. 84, Abs. E23 (1977).
Acevedo et al., "Immunohistochemical Localization of a Choriogonadotropin-Like Protein in Bacteria Isolated from Cancer Patients", Cancer, 41:1217–1229 (1978).
Gosslau et al., "Enzyme-Linked Immunosorbent Microassay for Quantification of Specific Antibodies to Collagen Type I, II, III", J. Immun. Meth. 29:71–77 (1979).
Maruo et al., "Studies on Choriogonadotropin from a Microorganism", The Endocrine Soc., 61st Ann. Meeting, Abst. 951 (1979).
Rennard et al., "Enzyme-Linked Immunoassay (ELISA) for Connective Tissue Components", Anal. Biochem., 104:205–214 (1980).

Primary Examiner—Sam Rosen
Attorney, Agent, or Firm—Dunlap, Codding, Peterson & Lee

[57] ABSTRACT

A method of detecting the presence of first antibodies against a chorionic gonadotropin-like substance in a first biological sample obtained from an organism other than domestic poultry. The first biological sample is contacted with a chorionic gonadotropin-like substance, preferably isolated from *Progenitor cryptocides* microorganism, which has been immobilized on a solid phase, under conditions permitting first antibody/chorionic gonadotropin-like substance binding. Unbound sample components are removed from the solid phase, and a plurality of second antibodies, each comprising an immunological conjugate of the first antibody, are contacted with the solid phase, under conditions permitting second antibody/first antibody binding. Unbound second antibodies are removed from the solid phase and the presence of chorionic gonadotropin-like substance/first antibody/second antibody complex, if any, is observed, as a measure of the presence of first antibodies in the first biological sample. Observation can be carried out photometrically by tagging the second antibodies with an enzyme labeling agent, such as alkaline phosphatase or horseradish peroxidase; enzyme degradation of a reagent added to the solid phase can be monitored via a color change reaction. The method can be adapted for use as a screening procedure for conditions associated with elevated levels of antibodies against a chorionic gonadotropin-like substance, such as active and prodromal neoplastic conditions.

26 Claims, No Drawings

4,876,192

DETECTION OF ANTIBODIES AGAINST A CHORIONIC GONADOTROPIN-LIKE SUBSTANCE

This is a continuation-in-part application of U.S. Ser. No. 778,847, filed Sept. 23, 1985, entitled: DETECTION OF ANTIBODIES AGAINST CHORIONIC GONADOTROPIN, now abandoned.

FIELD OF THE INVENTION

The present invention relates generally to immunological testing methods, and more particularly to such methods for detection of antibodies against a chorionic gonadotropin-like substance.

SUMMARY OF THE INVENTION

The present invention comprises a method of detecting the presence of first antibodies against a chorionic gonadotropin-like substance in a first biological sample obtained from an organism other than domestic poultry. The first biological sample is contacted with a chorionic gonadotropin-like substance which has been immobilized on a solid phase, under conditions which permit binding of first antibody to the chorionic gonadotropin-like substance. Unbound sample components are removed from the solid phase, and a plurality of second antibodies, each comprising an immunological conjugate of the first antibody, are contacted with the solid phase, under conditions permitting second antibody-first antibody binding. Unbound second antibodies are removed from the solid phase and the presence of chorionic gonadotropin-like substance/first antibody/second antibody complex, if any, is observed as a measure of the presence of first antibodies in the first biological sample. The method may be used as a means of screening for a condition characterized by an elevated level of antibodies against a chorionic gonadotropin-like substance and as a means of screening for an active or prodromal neoplastic condition.

DETAILED DESCRIPTION OF THE PREFERRED EMBODIMENTS

Chorionic gonadotropin is a hormone which normally is found only in pregnant females. It is produced by the placenta and its function is to stimulate the development of the gonads in the fetus. This hormone is not normally present in males or in non-pregnant females. Accordingly, antibodies against chorionic gonadotropin normally are not present in warm-blooded animals.

The microorganism *Progenitor cryptocides* is present in virtually all warm-blooded animals suffering from neoplastic conditions. V. Livingston and E. Alexander-Jackson, *Ann. N.Y. Acad. Sci.*, 174:636–654 (1970); and V. Livingston and A. M. Livingston, *Trans. N.Y. Acad. Sci.*, 36:569–582 (1974). This microorganism produces a substance like the hormone chorionic gonadotropin. H. Cohen and A. Strampp, *Proc. Soc. Exp. Biol. Med.*, 152:408–410 (1976); H. F. Acevado, M. Slifkin, G. R. Pouchet and M. Pardo, *Cancer*, 41:1217–1299 (1978); L. F. Affronti, L. Grow, R. Brumbough and K. Orton, Alesh. *Ann. Meeting Am. Soc. Micro.*, 1977, p. 84, New Orleans; T. Maruo, H. Cohen and S. S. Koide, Abst. 951, *The Endocrine Society*, 61st Annular Meeting, June 13–15, 1979; and P. H. Lange, T. R. Hakala and E. E. Fraley, *J. Urology*, 115:95–98 (1976).

The present invention is directed to a method for detecting antibodies against the chorionic gonadotropin-like substance, referred to herein as first antibodies, in a first biological sample. The first biological sample may be obtained from any organism or subject other than domestic poultry, and in many instances will comprise a test specimen comprising a bodily fluid, such as serum or urine, obtained from such a subject, which will be referred to as the first subject. Specifically, the first subject may be a warm-blooded animal such as a human. The method of the present invention may be used as a method of screening for a condition characterized by an elevated level of first antibodies in a subject, other than domestic poultry, from which a test specimen is taken and processed in accordance with the present invention.

In accordance with the method of the present invention, a chorionic gonadotropin-like substance, hereafter referred to as CG-like substance, which preferably is substantially pure, is immobilized on an immunologically inert solid phase, which preferably comprises a microtiter polystyrene plate, a polystyrene tube or Sepharose beads. The CG-like substance preferably is coated on the surface of the solid phase, and is held thereto in a fixed position. The coating step preferably is carried out by incubating a medium containing substantially pure CG-like substance for between about 24 hours and about 144 hours at a temperature between about 4° C. and about 5° C., with higher temperatures being preferred for shorter incubation periods. More specifically, the CG-like substance is included on the solid phase for about 72 hours at about 4° C.

The CG-like substance used in the method of the present invention preferably is isolated from the microorganism *Progenitor cryptocides*, ATCC No. 31,874. *Progenitor cryptocides* may be cultured, and an antigenic extract thereof prepared, in accordance with the procedure described in U.S. Pat. No. 4,410,510. This antigenic extract then may be purified, in order to produce the substantially pure antigen of *Progenitor cryptocides*, comprising substantially pure CG-like substance preferably by use of a chromatography and gel filtration techniques as described in Bahl, "Human Chorionic Gonadotropin: Purification and Physicochemical Properties", *J. Biological Chemistry*, 244, 567 (1969).

Unbound components from the medium containing the CG-like substance preferably are removed from the solid phase. This removal is carried out so as to leave undisturbed the CG-like substance which has been adsorbed on the surface of the solid phase. This removal preferably is carried out by washing the solid phase one or more times, and preferably three times, with an eluent to which the CG-like substance is substantially inert. A preferred eluent is PBS-Tween 20, a solution which may be prepared by mixing 8.0 g sodium chloride, 0.2 g potassium phosphate monobasic, 1.15 g sodium phosphate dibasic anhydrous, 0.2 g potassium chloride, 0.2 g sodium azide, and 0.5 ml Tween 20 (polyethylene [20] sorbitan monolaurate, available from Fisher Scientific Co., Fair Lawn, N.J.), diluted to 1 liter volume with distilled water and adjusted to a pH of 7.2. After removal step is completed, the solid phase is characterized by immobilized and preferably substantially pure CG-like substance formed on the surface thereof.

The first biological sample, or test specimen, is contacted with the solid phase, under conditions permitting, and preferably promoting, the binding of first antibodies and the CG-like substance. Preferably the first biological sample comprises serum from a subject to be tested, and more preferably the serum is diluted with PBS-BSA. The PBS-BSA diluent is prepared by mixing 8.0 g sodium chloride, 0.2 g potassium phosphate monobasic, 1.15 g sodium phosphate didasic anhydrous, 0.2 g potassium chloride, 0.2 g sodium azide, and 0.5 ml bovine serum albumin, at a concentration of 5 mg/ml; the mixture is diluted to a volume of 1 liter with distilled water and adjusted to a pH of 7.0 with 3M sodium hydroxide solution. A precision oscillating water bath, drained of water, may be used to promote reagent interaction.

The first biological sample most preferably is incubated in contact with the solid phase for between about 1 hour and about 4 hours, at a temperature of between about 20° C. and about 25° C., with higher temperatures being preferred for shorter incubation periods. Most preferably, the biological sample is incubated for about 2 hours at about 25° C. This contacting step results in binding of first antibodies, if any, in the first biological sample to the immobilized G-like substance on the solid phase, to form an immobilized CG-like substance/first antibody complex on the solid phase. Preferably, the CG-like substance is present on the solid phase in stoichiometric excess relationship to the number of first antibodies in the first biological sample, so that substantially all first antibodies in the first biological sample are caused to complex to the solid phase during the contacting step just described.

Unbound components of the first biological sample next are removed from the solid phase, preferably so as to retain the immobilized CG-like substance/first antibody complex, if any, in a substantially intact condition on the solid phase. This removal of unbound components of the first biological sample preferably is carried out by washing the solid phase one or more times, and preferably three times, with an eluent to which the solid phase, and any immobilized complex thereon, are substantially inert. A preferred eluent is PBS-Tween 20.

After unbound components from the first biological sample have been removed from the solid phase, the solid phase next is contacted with a plurality of second antibodies, each of which comprises an immunological conjugate of the first antibody, under conditions permitting, and preferably promoting, second antibody-first antibody binding. Preferably, the amount of second antibodies contacted with the solid phase is in stoichiometric excess relationship to the amount of first antibodies to be detected, so that second antibodies bind to substantially all of the immobilized CG-like substance/first antibody complex on the solid phase.

The selection of a second antibody for use in the method of the present invention will depend on the origin of the first biological sample in which first antibodies are to be detected. Preferably, the second antibodies comprise an immunoglobulin that will bind to the first antibodies in the first biological sample under study. When the first biological sample is of human origin, the second antibodies preferably comprise goat anti-human immunoglobulin.

Each second antibody preferably is tagged with a labeling agent, which is capable of degrading a reagent by means of an observable, and preferably quantifiable, degradation process. The labeling agent preferably comprises an enzyme, such as alkaline phosphatase or horseradish peroxidase, which is tagged to the second antibody by covalent bonding. When the labeling agent comprises an enzyme, the reagent preferably is degradable by the enzyme by a process which is accomplished by a perceptible color change, so that reagent degradation may be observed photometrically. Suitable degradable reagents include p-nitrophenol phosphate when the labeling agent is alkaline phosphatase, and o-phenylenediamine with hydrogen peroxide when the labeling agent is horseradish peroxidase. It should be noted that when the labeling agent is horseradish peroxidase, the eluent used to wash the solid phase, as described above, should not contain azide.

The second antibodies most preferably are incubated in contact with the solid phase for between about 1 hour and about 4 hours, at a temperature of between about 20° C. and about 25° C., with higher temperatures being preferred for shorter incubation periods. Most preferably, the second antibodies are incubated for about 2.5 hours at about 25° C. This contacting step results in binding of second antibodies to the immobilized CG-like substance/first antibody complex, if any, on the solid phase, to form an immobilized CG-like substance/first antibody/second antibody complex on the solid phase.

Preferably, the labeling agent is tagged to each second antibody before the second antibodies are contacted with the solid phase in accordance with the method of the present invention. However, it also is possible for the labeling agent to be tagged to the second antibodies after the second antibodies are contacted with the solid phase, and thus after the immobilized CG-like substance/first antibody/second antibody complex is formed on the solid phase.

Unbound second antibodies remaining after the contacting step just described next are removed from the solid phase, preferably so as to retain the immobilized CG-like substance/first antibody/second antibody complex, if any, in a substantially intact condition on the solid phase. The removal of unbound second antibodies preferably is carried out by washing the solid phase one or more times, and preferably three times, with an eluent to which the solid phase, and any immobilized complex thereon, are substantially inert. A preferred eluent is PBS-Tween 20.

After the unbound second antibodies are removed from the solid phase, the presence of CG-like substance/first antibody/second antibody complex, if any, is observed on the solid phase, as a measure of the presence of first antibodies in the first biological sample. When each second antibody is tagged with a labeling agent, as described above, the observation step is carried out by first contacting the solid phase with a reagent which is degradable by the labeling agent, and by thereafter observing the extent of degradation of the reagent.

As described above, it is preferred for the reagent to be degradable by the labeling agent by a process which produces a perceptible color change in the liquid medium or supernatant adjacent the solid phase. When the labeling agent comprises an enzyme such as alkaline phosphatase or horseradish peroxidase, it is preferred to incubate the reagent on the solid phase for between about 0.5 hour and about 1 hour, at a temperature of between about 20° C. and about 25° C. Most preferably, the reagent is incubated on the solid phase for about 0.5 hours at about 25° C.

Once the supernatant above the solid phase has reached the point of maximum absorbence, the optical density of the supernatant is determined photometrically, as a measure of the extent of the reagent degradation, and thus of the concentration of first antibodies in the first biological sample. If it is necessary or desirable to postpone the optical density measurement, the degradation reaction may be arrested by adding an appropriate counter-reagent to the supernatant above the solid phase. When the reagent is o-phenylenediamine, a preferred counter-reagent is 4N sulfuric acid solution; when the reagent is p-nitrophenol phosphate, a preferred counter-reagent is 3M sodium hydroxide solution.

In order to quantify the concentration of first antibodies in first biological sample, the reagent degradation associated with the first biological sample, as indicated by the optical density measurement described above, may be compared with the reagent degradation (i.e., optical density) associated with a second biological sample, containing a known concentration of first antibodies, after the second biological sample has been treated by the same procedures as the first biological sample.

When the method of the present invention is in use as a method of screening for a condition characterized by an elevated level of first antibodies against a CG-like substance, such as a prodromal or active neoplastic condition, it often will be desirable to compare the reagent degradation (i.e., optical density) associated with a first test specimen with the reagent degradation (i.e., optical density) associated with a second test specimen, obtained from a healthy second subject of the same species as the first subject providing the first test specimen, after the second test specimen has been treated by the same procedures as the first test specimen. Substantially higher reagent degradation, if any, in the first test specimen may be correlated with a condition characterized by an elevated level of first antibodies against a CG-like substance in the first subject. Such an elevated level of first antibodies indicates the likelihood of an active or prodromal neoplastic condition, and may dictate the commencement of further diagnostic and/or therapeutic measures with regard to the first subject.

In some instances it may be desired to compare the reagent degradation associated with the first test specimen with the reagent degradation associated with a second test specimen obtained from a second subject, of the same species as the first subject, and known to have a condition characterized by an elevated level of first antibodies, such as a neoplastic condition, after the second test specimen has been treated by the same procedures as the first test specimen. A level of reagent degradation in the first test specimen comparable to that of the second test specimen may indicate the presence of an elevated level of first antibodies, and thus the likelihood of an active or prodromal neoplastic condition in the first subject.

The following example illustrates how the method of the present invention will be practiced.

*Progenitor cryptocides* microorganism will be cultured in a culture medium and treated to isolate a purified extract residue containing CG-like substance, in accordance with the procedures described in U.S. Pat. No. 4,410,510. The purified extract residue then will be treated by chromatography on diethylaminoethyl Sephadex A-50, in accordance with the procedure set out in Bahl, "Human Chorionic Gonadotropin: Purification and Physicochemical Properties", *J. Biological Chemistry,* 244, 567 (1969). The fractions showing highest absorbance will be dialyzed and lyophilized. The recovered residue then will be dissolved in a buffer solution and applied to another column of diethylaminoethyl Sephadex A-50. The fractions showing highest absorbance then will be further purified and the residue subjected to gel filtration on Sephadex G-100. After further dialyzation and lyophilization, the recovered residue will comprise substantially pure *Progenitor cryptocides* CG-like substance.

The CG-like substance thus recovered will be dissolved in 0.1M acetic acid at a concentration of 2 mg/ml overnight at 4° C. The acetic acid solution of CG-like substance then will be diluted in a coating buffer solution, which will be prepared by mixing 8.4 g sodium bicarbonate, 29.2 g sodium chloride, and 0.2 g sodium azide, and diluting the mixture to 1 liter volume with distilled water, and adjusting the pH to 8.3. The final concentration of CG-like substance in the coating buffer solution will be between 100 $\mu$g/ml and 500 $\mu$g/ml, with a 100 $\mu$g/ml concentration preferred. 200 microliters of the CG-like substance/acetic acid/coating buffer preparation will be added to each well of one or more polyvinyl or polystyrene microtiter plates, which are available from Cooke Laboratory Products, Alexandria, Va. The plates will be sealed to prevent dessication and will be stored at 4° C. for at least 24 hours. Adsorption of CG-like substance to the wells of the plates may proceed for as long as 6 days.

After the adsorption step is complete, the CG-like substance solution will be removed from the wells by inverting each plate and abruptly flicking each plate. After any residual liquid on the plates is blotted from the top of each plate, 0.2 ml of a PBS-Tween 20 eluent will be added to each well of each plate. The flicking and washing procedure will be repeated 3 times. After the third wash and subsequent flicking, the plates will be ready for treatment with a first biological sample from a human subject, as well as with control specimens.

0.2 ml of serum obtained from a subject under study will be diluted with PBS-BSA to a serum/PBS-BSA volume ratio of 2. 0.2 ml of the diluted test serum will be added to appropriate wells and allowed to bind to the CG-like substance therein. The plates will be rocked continuously at 25° C. and the diluted serum sample or samples retained in the wells for 120 minutes. Each plate will then be flicked to remove unbound sample components, and then washed 3 times with PBS-Tween 20 by the washing and flicking procedure described above.

Alkaline phosphatase, type VII from calf intestine, which may be obtained from Sigma Chemical Company, St. Louis, Missouri, will be conjugated with goat anti-human immunoglobulin, which may be purchased from Miles Biochemical, Elkhart, Ind., in accordance with the procedures described in Voller et al., "Enzyme-Immunoassays for Antibodies in Measles, Cytomegalovirus Infections and After Rubella Vaccination", *Br. J. Exp. Path.,* 57, 243 (1976). The antiserum will be diluted in PBS-BSA in PBS-BSA/antiserum volume ratio of between 500 and 1500.

If horseradish peroxidase is used in lieu of alkaline phosphatase as the labeling agent, the horseradish peroxidase may be obtained from Miles Biochemical, Elkhart, Ind. Conjugates of horseradish peroxidase to goat anti-human immunoglobulin will be prepared by use of the two-step procedure described in Avreamas et al., *Immunochemistry,* 8, 1175 (1971). The horseradish peroxidase-conjugated immunoglobulin will be diluted in PBS-BSA as described above.

0.2 ml of diluted, enzyme-conjugated goat anti-human immunoglobulin will be added to one or more of the wells previously treated with the test sample. The wells will be incubated with the antiserum at 25° C. for 120 minutes, while undergoing a continuous rocking motion. The antiserum will then be removed, and the wells washed three times with PBS-Tween 20 by the washing and flicking procedure described above.

If the labeling agent is alkaline phosphatase, 0.2 ml of p-nitrophenol phosphate reagent solution will be added to one or more of the wells previously treated with antiserum. The reagent solution is prepared by dissolving 5 mg of p-nitrophenyl phosphate, available from Sigma Chemical Company, St. Louis, Mo., in 1 ml of 1.0M diethanol amine buffer. This buffer is prepared by mixing 97 ml diethenol amine with 0.2 g sodium azide, and 0.1 g magnesium chloride hexahydrate, diluting to a volume of 1 liter with distilled water and adjusting the pH to 9.8. The reagent solution should be stored in a dark bottle at 4° C. Once the enzyme degradation reaction in each well has reached maximum absorbance, the reaction will be arrested by adding 0.05 ml of 3M sodium hydroxide to each well previously treated with p-nitrophenol phosphate.

If the labeling agent is horseradish peroxidase, 0.2 ml of o-phenylenediamine reagent solution will be added to one or more wells previously treated with antiserum as described above. The reagent solution consists of a solution of o-phenylenediamine dissolved in methanol at a concentration of 10 mg/ml, which is available from Aldrich Chemical Company, Milwaukee, Wisconsin. The o-phenylenediamine solution will be diluted with a 0.03% solution of hydrogen peroxide in distilled water at an o-phenylenediamine solution/hydrogen peroxide solution volume ratio of 1:100, to form the reagent solution. A fresh reagent solution should be prepared daily. The enzyme degradation reaction in each well will be arrested at the point of maximum absorbance by adding 0.05 ml 4 N sulfuric acid to each well previously treated with o-phenylenediamine reagent solution.

After the enzyme degradation reaction has been arrested, the entire supernatant fluid, comprising 0.25 ml volume, will be removed from each well, diluted to 1.0 ml with the diethanol amine buffer described above, and the optical density of the supernatant determined at 420 nm.

For control purposes, the procedures described above will be used to test a normal serum sample in place of the sample from the subject tested, and a sample of a reference serum from a subject having an elevated level of CG-like substance in place of the sample from the subject to be tested. Also for control purposes, binding of the enzyme-conjugated antiserum to CG-like substance in the absence of serum from the test subject will be observed. Likewise, addition of the labeling agent reagent to wells not treated with enzyme-conjugated antiserum, but otherwise treated by the same procedures described above, will be observed for control purposes.

Serum endpoints will be determined using three different methods: endpoint equal to twice the average value obtained with the control (normal human serum); the first titer to be significantly above the control, working from the most dilute to the most concentrated specimens; and the intercept on the abscissa obtained by a linear line regression in a plot of absorbance at 420 nm (ordinate) versus serum dilution (abscissa). Means should correlate well between the first and second methods for determining endpoint. Endpoints determined by linear line regression should be markedly lower than those obtained by either of the other two methods. Serum endpoints will be determined using the first significant titer procedure in drug studies.

Changes may be made in the construction, operation, arrangement and order of the various parts, elements, steps and procedures described herein without departing from the spirit and scope of the invention defined in the following claims.

What is claimed is:

1. A method of screening for a condition characterized by an elevated level of first antibodies against a chorionic gonadotropin-like substance, in a first subject other than domestic poultry, comprising:
   contacting a first test specimen from the first subject with chorionic gonadotropin-like substance immobilized on a solid phase, under conditions permitting first antibody-chorionic gonadotropin-like substance binding;
   removing unbound specimen components from the solid phase;
   contacting a plurality of second antibodies, each comprising an immunological conjugate of the first antibody, with the solid phase, under conditions permitting second antibody/first antibody binding;
   removing unbound second antibodies from the solid phase; and
   observing the presence of chorionic gonadotropin-like substance/first antibody/second antibody complex, if any, on the solid phase.

2. The method of claim 1 in which the chorionic gonadotropin-like substance has been isolated from *Progenitor cryptocides*.

3. The method of claim 1 in which each second antibody is tagged with a labeling agent and in which the observation step comprises:
   contacting the solid phase with a reagent which is degradable by the labeling agent; and
   observing the extent of degradation of the reagent.

4. The method of claim 3 in which the labeling agent is tagged to each second antibody before the second antibodies are contacted with the solid phase.

5. The method of claim 3 in which the labeling agent is tagged to each second antibody after the second antibodies are contacted with the solid phase.

6. The method of claim 3 in which the reagent degradation is observed photometrically.

7. The method of claim 3 in which the labeling agent is alkaline phosphotase.

8. The method of claim 3 in which the labeling agent is horseradish peroxidase.

9. The method of claim 3 further comprising:
   comparing the reagent degradation associated with the first test specimen with the reagent degradation associated with a second test specimen, comprising a known concentration of first antibodies, as a result of treatment of the second test specimen by the same procedures as the first test specimen.

10. The method of claim 3 further comprising:
    comparing the reagent degradation associated with the first test specimen with the reagent degradation associated with a second test specimen, obtained from a healthy second subject of the same species as the first subject, as a result of treatment of the second test specimen by the same procedures as the first test specimen.

11. The method of claim 3, further comprising:

correlating a substantially higher reagent degradation, if any, in the first test specimen, as compared to the second test specimen, with a condition characterized by an elevated level of first antibodies against a chorionic gonadotropin-like substance in the first subject.

12. The method of claim 3 further comprising: comparing the reagent degradation associated with the first test specimen with the reagent degradation associated with a second test specimen, obtained from a second subject of the same species as the first subject and having a condition characterized by an elevated level of first antibodies, as a result of treatment of the second test specimen by the same procedures as the first test specimen.

13. The method of claim 12, further comprising: correlating a comparable level of reagent degradation, if any, in the first test specimen, as compared to the second test specimen, with a condition characterized by an elevated level of first antibodies against a chorionic gonadotropin-like substance in the first subject.

14. A method of screening for an active or prodromal neoplastic condition in a first subject other than domestic poultry, comprising:
   contacting a first test specimen from the first subject with a chorionic gonadotropin-like substance immobilized on a solid phase, under conditions permitting the immobilized chorionic gonadotropin-like substance to bind with first antibodies against chorionic gonadotropin-like substance, if any, in the test specimens;
   removing unbound specimen components from the solid phase;
   contacting a plurality of second antibodies, each comprising an immunological conjugate of the first antibody, with the solid phase, under conditions permitting second antibody/first antibody binding;
   removing unbound second antibodies from the solid phase; and
   observing the presence of chorionic gonadotropin-like substance/first antibody/second antibody complex, if any, on the solid phase.

15. The method of claim 14 in which the chorionic gonadotropin-like substance has been isolated from *Progenitor cryptocides*.

16. The method of claim 14 in which each second antibody is tagged with a labeling agent and in which the observation step comprises:
   contacting the solid phase with a reagent which is degradable by the labeling agent; and
   observing the extent of degradation of the reagent.

17. The method of claim 16 in which the labeling agent is tagged to each second antibody before the second antibodies are contacted with the solid phase.

18. The method of claim 16 in which the labeling agent is tagged to each second antibody after the second antibodies are contacted with the solid phase.

19. The method of claim 16 in which the reagent degradation is observed photometrically.

20. The method of claim 16 in which the labeling agent is alkaline phosphotase.

21. The method of claim 16 in which the labeling agent is horseradish peroxidase.

22. The method of claim 16 further comprising:
   comparing the reagent degradation associated with the first test specimen with the reagent degradation associated with a second test specimen, comprising a known concentration of first antibodies, as a result of treatment of the second test specimen by the same procedures as the first test specimen.

23. The method of claim 16 further comprising:
   comparing the reagent degradation associated with the first test specimen with the reagent degradation associated with a second test specimen obtained from a healthy second subject of the same species as the first subject, as a result of treatment of the second test specimen by the same procedures as the first test specimen.

24. The method of claim 23, further comprising:
   correlating a substantially higher reagent degradation, if any, in the first test specimen, as compared to the second test specimen, with the likelihood of the presence of an active or prodomal neoplastic condition in the first subject.

25. The method of claim 16 further comprising:
   comparing the reagent degradation associated with the first test specimen with the reagent degradation associated with a second test specimen obtained from a second subject of the same species as the first subject and suffering from a neoplastic condition as a result of treatment of the second test specimen by the same procedures as the first test specimen.

26. The method of claim 25, further comprising:
   correlating a comparable level of reagent degradation, if any, in the first test specimen, as compared to the second test specimen, with the likelihood of the presence of an active or prodomal neoplastic condition in the first subject.

* * * * *

UNITED STATES PATENT AND TRADEMARK OFFICE
CERTIFICATE OF CORRECTION

PATENT NO. : 4,876,192

DATED : October 24, 1989

INVENTOR(S) : Donald E. Weder, et al.

It is certified that error appears in the above-identified patent and that said Letters Patent is hereby corrected as shown below:

Column 1, line 60, "1299" should be --1229--.

Column 1, line 64, "Annular" should be --Annual--.

Column 2, line 29, "included" should be --incubated--.

Column 3, line 19, "G-like" should be --CG-like--.

Signed and Sealed this

Twelfth Day of February, 1991

Attest:

HARRY F. MANBECK, JR.

*Attesting Officer*  *Commissioner of Patents and Trademarks*